US008070489B2

(12) United States Patent
Massad

(10) Patent No.: US 8,070,489 B2
(45) Date of Patent: Dec. 6, 2011

(54) INTEGRATED MODULAR DENTAL MEASURING APPARATUS AND METHOD FOR DENTURES

(75) Inventor: Joseph J. Massad, Tulsa, OK (US)

(73) Assignee: Global Dental Impression Trays, Inc., Tulsa, OK (US)

( * ) Notice: Subject to any disclaimer, the term of this patent is extended or adjusted under 35 U.S.C. 154(b) by 320 days.

(21) Appl. No.: 12/393,390

(22) Filed: Feb. 26, 2009

(65) Prior Publication Data

US 2009/0246729 A1 Oct. 1, 2009

Related U.S. Application Data

(60) Provisional application No. 61/040,457, filed on Mar. 28, 2008.

(51) Int. Cl.
*A61J 9/00* (2006.01)
(52) U.S. Cl. .......................................................... 433/71
(58) Field of Classification Search .................. 433/68, 433/69, 70, 71
See application file for complete search history.

(56) References Cited

U.S. PATENT DOCUMENTS

| | | | | |
|---|---|---|---|---|
| 1,734,398 A | * | 11/1929 | Phillips | 433/69 |
| 2,183,512 A | | 12/1939 | Brenner | |
| 2,255,267 A | * | 9/1941 | Moran | 433/69 |
| 2,481,203 A | * | 9/1949 | Nicole | 433/69 |
| 2,863,216 A | | 12/1958 | Lichtman et al. | |
| 2,994,957 A | * | 8/1961 | McLeod | 433/69 |
| 3,161,956 A | * | 12/1964 | Van Court et al. | 433/71 |
| 4,439,151 A | * | 3/1984 | Whelan | 433/60 |
| 4,522,591 A | * | 6/1985 | Braun et al. | 433/60 |
| 4,964,769 A | | 10/1990 | Hass | |
| 5,007,830 A | | 4/1991 | Joffe | |
| 5,076,785 A | * | 12/1991 | Tsai | 433/46 |
| 5,186,624 A | * | 2/1993 | Gottsleben | 433/69 |
| 5,188,529 A | | 2/1993 | Luth | |
| 5,336,087 A | | 8/1994 | Vogel et al. | |
| 5,722,828 A | | 3/1998 | Halstrom | |
| 5,752,826 A | * | 5/1998 | Andreiko | 433/41 |
| 5,971,756 A | | 10/1999 | Fjelstad | |
| 5,989,023 A | | 11/1999 | Summer et al. | |
| 6,106,285 A | * | 8/2000 | Kwak | 433/68 |
| 6,152,730 A | * | 11/2000 | Wildman | 433/68 |
| 2006/0127839 A1 | * | 6/2006 | Sellmann | 433/69 |
| 2007/0148612 A1 | * | 6/2007 | Massad | 433/37 |
| 2007/0231774 A1 | | 10/2007 | Massad | |

FOREIGN PATENT DOCUMENTS

EP 0950384 10/1999

* cited by examiner

*Primary Examiner* — John P Leubecker
*Assistant Examiner* — Christopher Sponheimer
(74) *Attorney, Agent, or Firm* — Head, Johnson & Kachigian, P.C.

(57) ABSTRACT

An integrated modular dental measuring apparatus and method of use for producing edentulous dentures, each including a lower dental tray having a removable modular contact plate with an upwardly extending shoulder surrounding a tapered opening, a ball nut retained in the tapered opening, and a post adjustably secured to the ball nut. A modular striking plate may be removably attached to an upper dental tray or an integrated striking sector on a bottom surface of the upper dental tray is utilized to accurately obtain an established occlusal vertical and centric relation positions. The contact plate and striking plate are each configured as snap-in components to the respective trays. Additionally, the contact plate may be utilized as a spacer between the dental trays once the post and ball nut are removed. Finally, the contact plate and striking plate may be removed for functional positioning and esthetic blue printing measurements.

17 Claims, 13 Drawing Sheets

INTEGRATED MODULAR DENTAL MEASURING APPARATUS AND METHOD FOR DENTURES

CROSS-REFERENCE TO RELATED APPLICATIONS

This application claims priority to U.S. Provisional Application No. 61/040,457, filed Mar. 28, 2008, which is herein incorporated by reference.

BACKGROUND OF THE INVENTION

1. Field of the Invention

This invention relates generally to an apparatus for obtaining accurate measurements and calibrations in order to produce dentures for edentulous patients and a method of using the same, and more particularly to an integrated modular dental measuring apparatus, the use of which will reduce the number of visits required in order to obtain the required measurements and calibrations while not eliminating detail of records in order to produce a set of dentures, wherein the dental trays thereof may be converted to multiple uses.

2. Description of the Related Art

Treatment of patients that are missing teeth is often accomplished by complete dentures including an upper denture and a lower denture or accomplished by partial dentures. Prior to making new or replacement dentures, multiple measurements and calibrations are taken of the patient and the patient's mouth and any existing dental prostheses are recorded. Additionally, appropriate measurements are taken to verify the proper fit and relationships of the dental prostheses not only with the oral cavity but with each other.

Ideally, dentures should mate with the mouth and function with existing mouth tissue. Poor fitting dentures can cause mouth soreness and can negatively influence a patient's facial appearance and even a patient's diet. The production of accurate partial or complete dentures requires multiple measurements and multiple calibrations.

In existing practice, an impression is used to create an imprinted likeness of a jaw, any teeth and any implants, along with gingiva areas of the oral cavity. An upper tray and a lower tray are selected by size and filled with impression material, such as a resin. From this impression, an acrylic or stone cast is made. Additional measurements and calibrations include establishing the centric position or repeatable horizontal and vertical spacing. Identifying and measuring appropriate occlusal vertical dimensions and centric relation positions during treatment of edentulous patients is also necessary for predictable and successful application of dental prostheses.

Additional measurements include esthetic blue printing to accommodate the shape of the patient's upper lip and mouth. This imprint will guide the laboratory in both cosmetic and tooth set up. Additionally, a set of measurements known as "neutral zone technique" will accommodate measurement of the functional tongue, cheek and lip positioning of the patient. Finally, an articulator or other similar device is often utilized to determine the position of the arches with respect to the jaws of the patient.

It is therefore desirable to provide an integrated modular dental measuring apparatus and method for dentures for obtaining a series of measurements and calibrations of a patient to reduce the number of visits that the patient is required to make to the dental professional.

It is further desirable to provide an integrated modular dental measuring apparatus and method for dentures that enable multiple measurements and calibrations to be made in a single fitting in order to produce a set of dentures.

It is still further desirable to provide an integrated modular dental measuring apparatus and method for dentures that reduce the required inventory of different types of dental trays which are necessary to produce a set of dentures.

It is yet further desirable to provide an integrated modular dental measuring apparatus and method for dentures that is convertible in order to be used for different measurement and calibration functions.

SUMMARY OF THE INVENTION

In general, in a first aspect, the invention relates to an integrated modular dental measuring apparatus comprising a lower dental tray having an upwardly extending ridge, where the ridge has periodic gaps; a contact plate with outwardly extending tabs sized and spaced such that the tabs fit within the gaps in the ridge of the lower dental tray and allow the contact plate to snap onto the lower dental tray; a tapered opening in the contact plate; a ball nut retained in the tapered opening; a post adjustably secured to the ball nut; an upper dental tray having a downwardly extending ridge, where the ridge has periodic gaps; and a striking plate with outwardly extending tabs sized and spaced such that the tabs fit within the gaps in the ridge of the upper dental tray and allow the striking plate to snap onto the upper dental tray. The combination of the contact plate, the ball nut, and the post with the striking plate cooperate to obtain occlusal vertical dimension, centric relation position, and other dental measurements.

The contact plate and the striking plate may each be of uniform size such that one size contact plate fits on all sizes of lower dental trays and one size striking plate fits on all sizes of upper dental trays. The contact plate may function as a spacer when the post and the ball nut are removed. The dental measuring apparatus may be used by snapping the contact plate onto the lower dental tray; retaining the ball nut in the tapered opening in the contact plate; securing the post to the ball nut so that the length of the post and the angular position of the post may be altered; snapping the striking plate onto the upper dental tray, and utilizing the lower dental tray and the upper dental tray to accurately obtain and establish occlusal, vertical, and horizontal positions. Furthermore, the post and the ball nut may be removed and the contact plate may be used as a spacer.

The integrated modular dental measuring apparatus can also include an upper impression tray having a channel for receipt of the ridge of the lower dental tray and a lower impression tray having a channel for receipt of the ridge on the upper dental tray. The channel of the upper impression tray may include stubs sized to frictionally engage the gaps in the ridge of the lower dental tray, while the channel of the lower impression tray may include stubs sized to frictionally engage the gaps in the ridge of the upper dental tray. The upper impression tray and the lower impression tray may be formed of any suitable moldable dental composition, such as wax or resin.

In general, in a second aspect, the invention relates to an integrated modular dental measuring apparatus comprising a lower dental tray having a plurality of apertures along an intaglio channel; a contact plate with outwardly extending tabs sized and spaced such that the tabs fit within the apertures of the lower dental tray and allow the contact plate to snap onto the lower dental tray; a tapered opening in the contact plate; a ball nut retained in the tapered opening and a post adjustably secured to the ball nut and an upper dental tray having a substantially planar striking sector. The combination of the contact plate, the ball nut, and the post with the striking sector cooperate to obtain occlusal vertical dimension, centric relation position, and other dental measurements.

The contact plate may function as a spacer when the post and the ball nut are removed. In addition, the upper dental tray may include an intaglio channel and an upwardly contoured palatal ledge spanning the intaglio channel. The palatal ledge includes an upper surface having a smooth, posterior portion and an anterior portion having a plurality of substantially vertical and parallel fins. The palatal ledge also includes a bottom surface having a substantially curved posterior portion and the striking sector near an anterior portion.

In general, in a third aspect, the invention relates to a method of using a dental measuring apparatus by way of snapping a contact plate onto a lower dental tray; retaining a ball nut in a tapered opening in the contact plate; securing a post to the ball nut so that the length of the post and the angular position of the post may be altered; and cooperating the contact plate, the nut, and the post respectively secured to the lower dental tray with a striking sector on the upper dental tray to accurately obtain and establish occlusal vertical dimension, centric relation position, and other dental measurements. The lower dental tray includes periodic gaps and the contact plate has outwardly extending tabs sized and spaced such that the tabs fit within the gaps in the ridge of the lower dental tray and allow the contact plate to snap onto the lower dental tray.

The striking sector on the upper dental tray may be a removably attachable striking plate, which may be snapped onto the upper dental tray. The upper dental tray can include a downwardly extending ridge with periodic gaps, while the striking plate has outwardly extending tabs sized and spaced such that the tabs fit within the gaps in the ridge of the upper dental. The striking plate may be removed from the upper dental tray for use in recognizing the upper lip and mouth of a patient during esthetic blue printing.

In addition, the post and the ball nut may be removed from the contact plate, allowing the contact plate to be used as a spacer between the lower dental tray and the upper dental tray. Further, the contact plate may be removed from the lower dental tray for determining functional position.

Other advantages and features will be apparent from the following description and from the claims.

DETAILED DESCRIPTION OF THE INVENTION

The apparatuses and methods discussed herein are merely illustrative of specific manners in which to make and use this invention and are not to be interpreted as limiting in scope.

While the apparatuses and methods have been described with a certain degree of particularity, it is to be noted that many modifications may be made in the details of the construction and the arrangement of the apparatuses and components without departing from the spirit and scope of this disclosure. It is understood that the apparatuses and methods are not limited to the embodiments set forth herein for purposes of exemplification.

Three sets of trays may be used to take multiple measurements and calibrations in a single visit to a dentist or technician. The first set of dental trays may be used to take an impression of the patient's jaw, any teeth, and any implants, along with gingiva areas of the oral cavity. Such dental trays and their use is explained in detail in Applicant's co-pending patent application Ser. Nos. 11/680,992 and 60/986,142, which are incorporated herein by reference.

Figure 6:
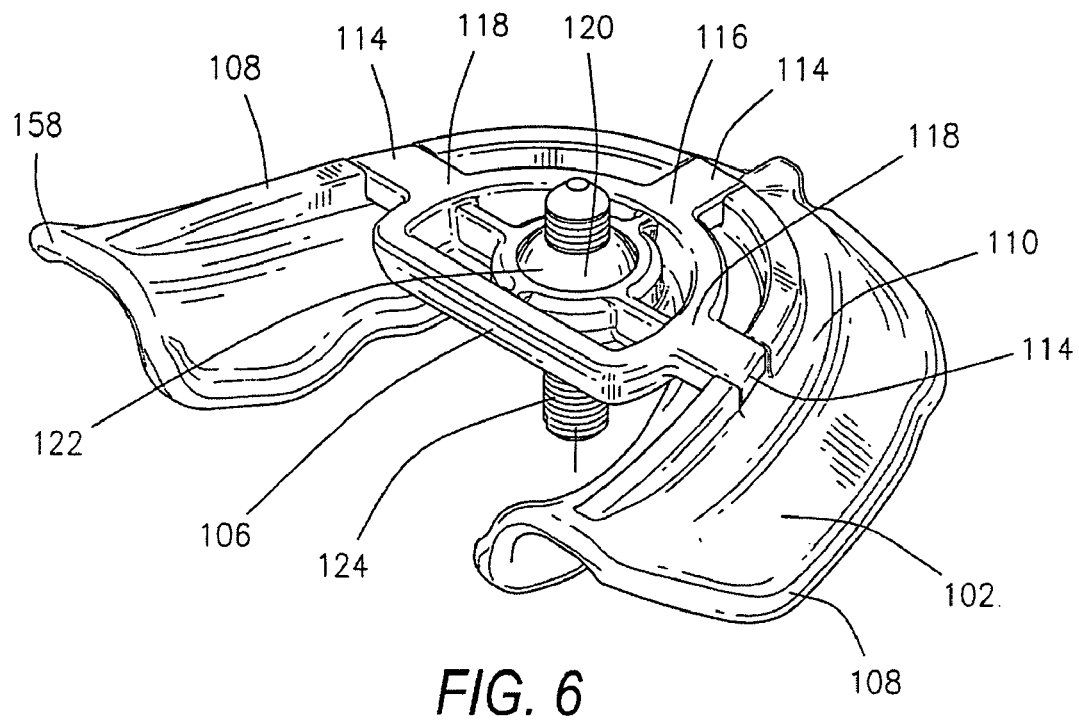
FIG. 6 is a top perspective view of an example of a lower dental tray with a contact plate inserted thereon in accordance with an illustrative embodiment of the integrated modular dental measuring apparatus and method for dentures disclosed herein.
Figure 7:
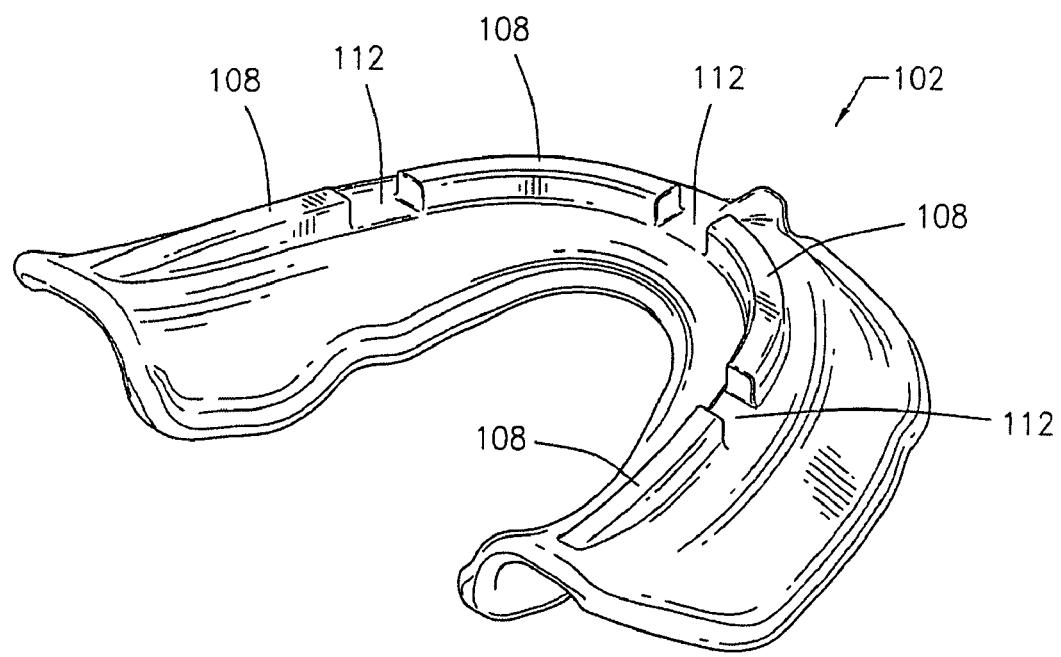
FIG. 7 is a top perspective view of the lower dental tray shown in FIG. 6 with the contact plate removed.

Once the first set of dental trays has been utilized and removed, a second set of dental trays may be utilized for establishing the occlusal vertical dimensions and centric relation positions. Referring to the figures of the drawings, wherein like numerals of reference designate like elements throughout the several views, and initially to FIGS. 1 through 5, the second set of dental trays comprises an integrated modular dental measuring apparatus 100 having a lower dental tray 102 and an upper dental tray 104. The lower dental tray 102 includes a contact plate 106 removably secured to and attached to the lower dental tray 102. The lower dental tray 102 may include an upwardly extending ridge 108 running along a top surface 110. The ridge 108 has small slots or gaps 112 located at various points. Into these slots or gaps 112 fit a plurality of tabs 114 extending outward from the contact plate 106 on corresponding locations, such as the anterior portion 116 and side portions 118 of the contact plate 106. The tabs 114 may be slightly larger than the slots or gaps 112 so that the tabs 114 snugly fit therein. Thus, the contact plate 106 snap fits into place on the lower dental tray 102. Accordingly, the lower dental tray 102 may be used with or without the contact plate 106. FIG. 6 illustrates the lower dental tray 102 with the contact plate 106 attached thereto apart from the upper dental tray 104 to be described herein. FIG. 7 illustrates the lower dental tray 102 with the contact plate 106 removed, with the ridge 108 and slots or gaps 112 visible. As exemplified throughout the Figures, the lower dental tray 102 may be arcuate in form and may include a border 158 along its terminal periphery. The border 158 has a predetermined diameter such that the diameter of the border 158 is slightly larger that the thickness of the lower dental tray 102.

The lower dental tray 102 may be made in varying sizes to accommodate different sizes of mouths. For example, the lower dental tray 102 may come in small, medium and large sizes. However, every size of lower dental tray 102 has the same size ridge 108 and slots or gaps 112 at the same locations, so that one size of contact plate 106 fits into all sizes of lower dental tray 102 thereby reducing the required inventory of contact plates 106.

The contact plate 106 includes a tapered opening 120, and a ball nut 122 is retained in the tapered opening 120, which permits the ball nut 122 to rotate within the tapered opening 120. The ball nut 122 may be spherical in shape and may have a cylindrical bore through a diameter thereof. A post 124 is adjustably secured to the ball nut 122 so that the length and the angular position of the post 124 may be altered.

Figure 8:
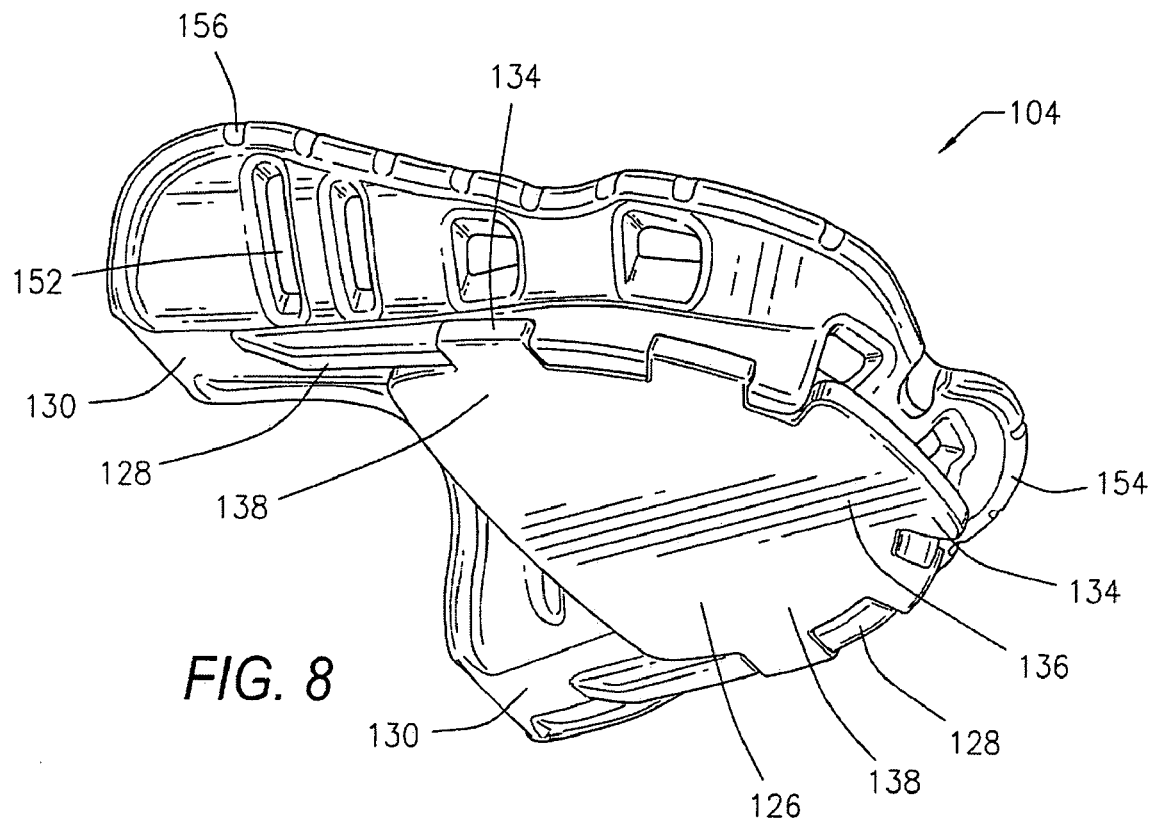
FIG. 8 is a bottom perspective view of an example of an upper dental tray with a striking plate inserted thereon in accordance with an illustrative embodiment of the integrated modular dental measuring apparatus and method for dentures disclosed herein.
Figure 9:
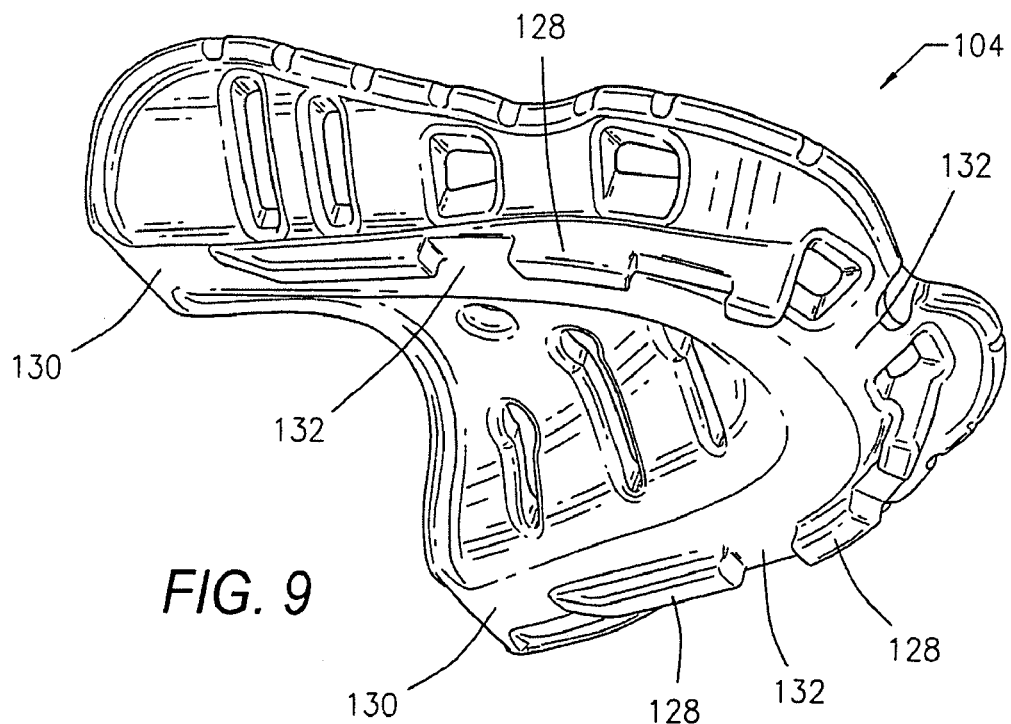
FIG. 9 is a bottom perspective view of the upper dental tray as shown in FIG. 8 with the striking plate removed.
Figure 10:
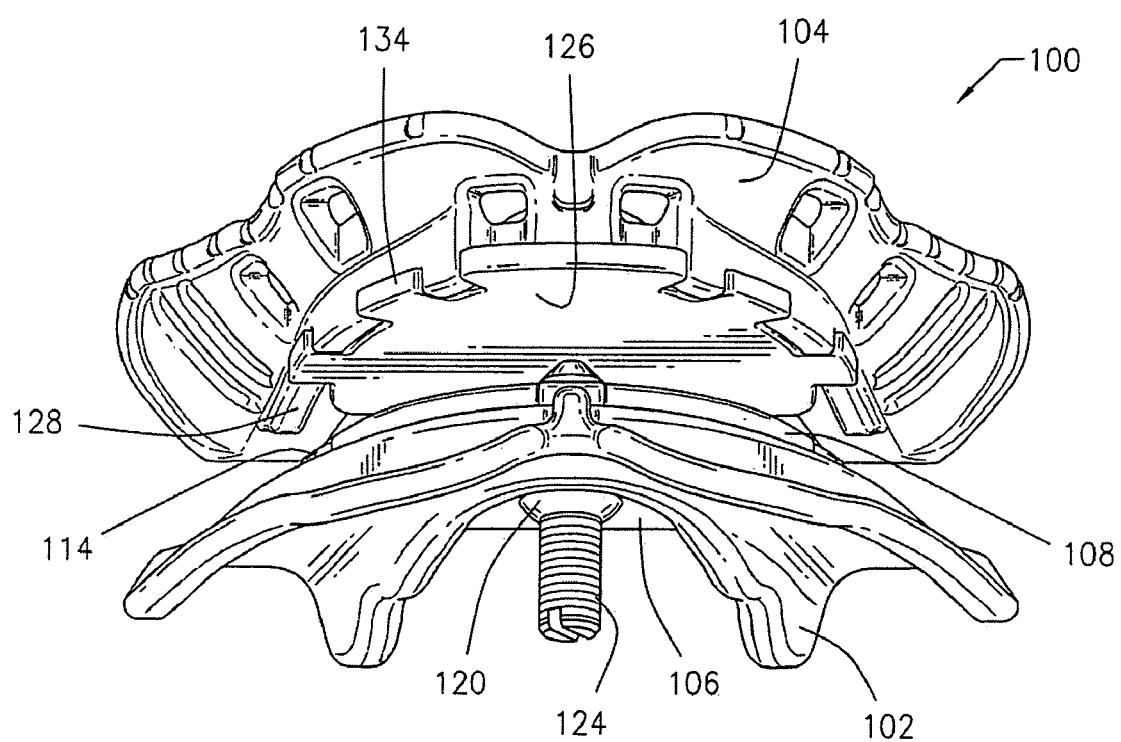
FIG. 10 is a perspective view of the integrated modular dental measuring apparatus utilized to obtain and establish proper occlusal vertical and centric relation positions of a patient in accordance with an illustrative embodiment of the integrated modular dental measuring apparatus and method for dentures disclosed herein.

Returning to consideration of FIGS. 1 through 5, the upper dental tray 104 includes a striking plate 126 removably secured to and attached to the upper dental tray 104. The upper dental tray 104 may include a downwardly extending ridge 128 running along a bottom surface 130. The ridge 130 has small slots or gaps 132 at various points. Into these slots or gaps 132 fit tabs 134 extending outward from the striking plate 126 at corresponding locations, such as from the anterior portion 136 and side portions 138 of the striking plate 126 as illustrated in FIGS. 8 and 10. The tabs 134 may be slightly larger than the slots or gaps 132 so they snugly fit therein. Thus, the striking plate 126 snap fits into place on the upper dental tray 104. FIG. 8 illustrates the upper dental tray 104 with the striking plate 126 attached thereto apart from the lower tray 102, while FIG. 9 illustrates the upper dental tray 104 with the striking plate 126 removed, with the ridge 128 and gaps 132 visible.

Figure 1:
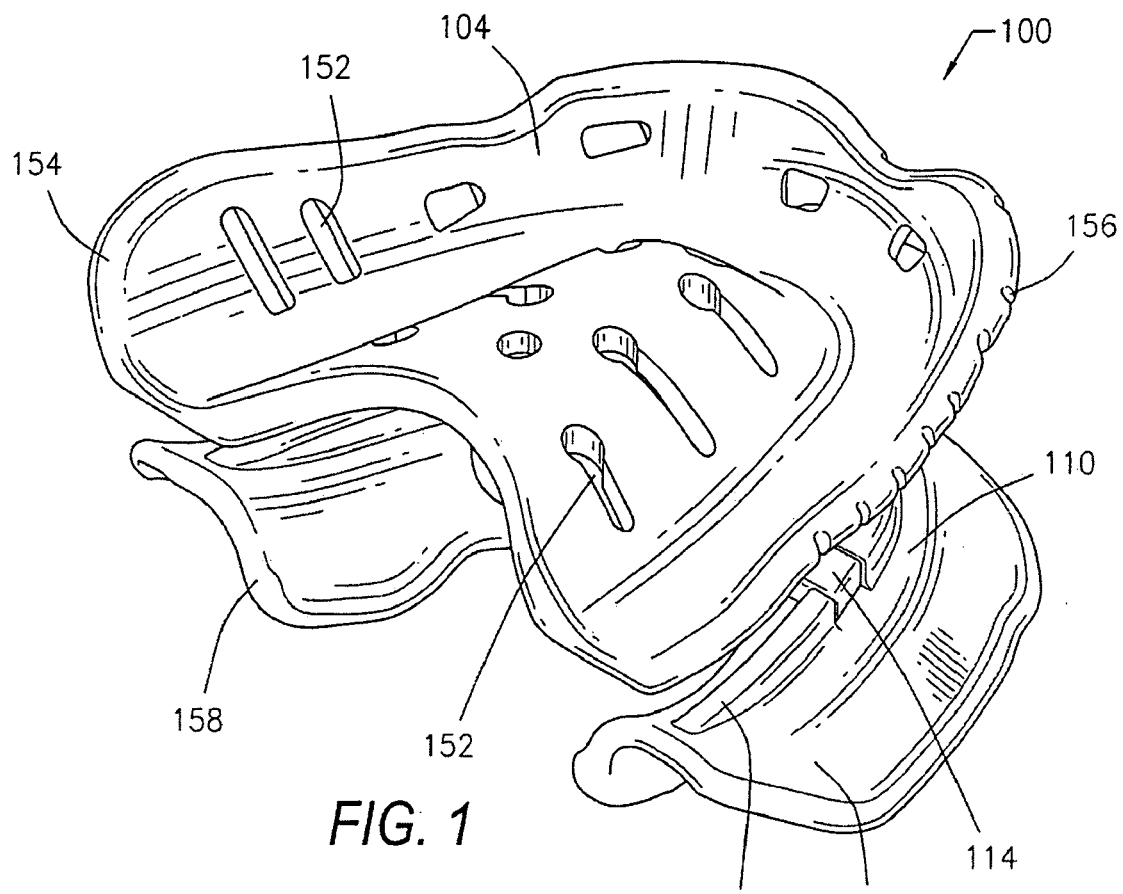
FIG. 1 is a perspective view of an example of an integrated modular dental measuring apparatus in accordance with an illustrative embodiment of the integrated modular dental measuring apparatus and method of dentures disclosed herein.
Figure 2:
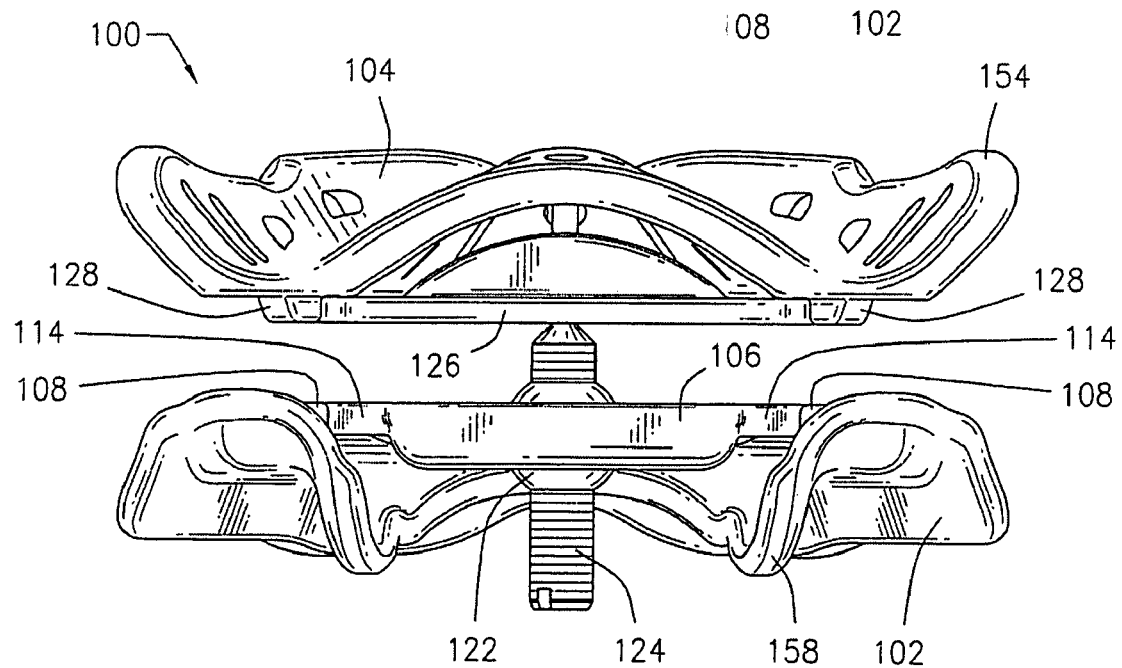
FIG. 2 is a posterior perspective view of the integrated modular dental measuring apparatus shown in FIG. 1.
Figure 3:
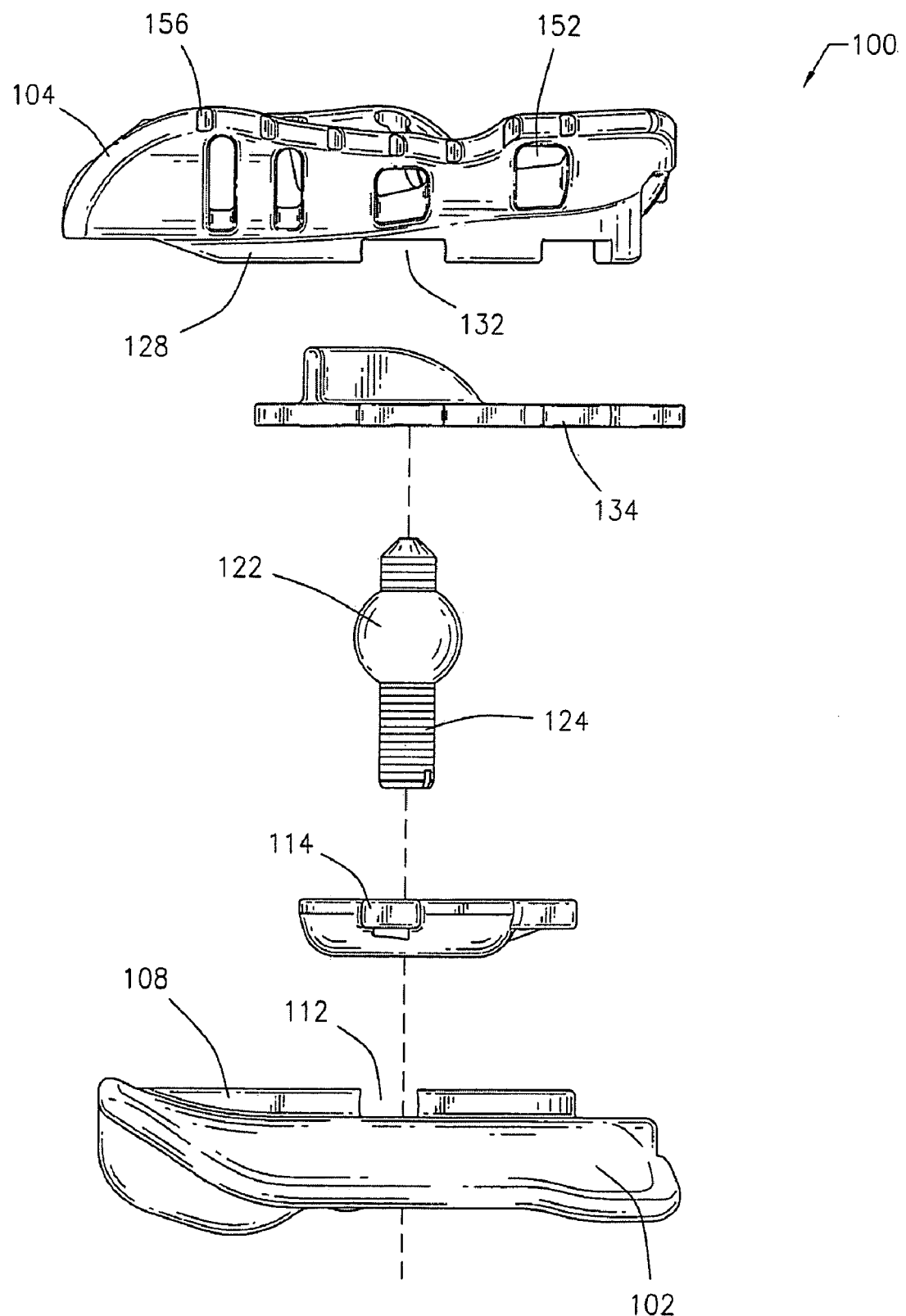
FIG. 3 is an exploded perspective view of the integrated modular dental measuring apparatus shown in FIG. 1.
Figure 4:
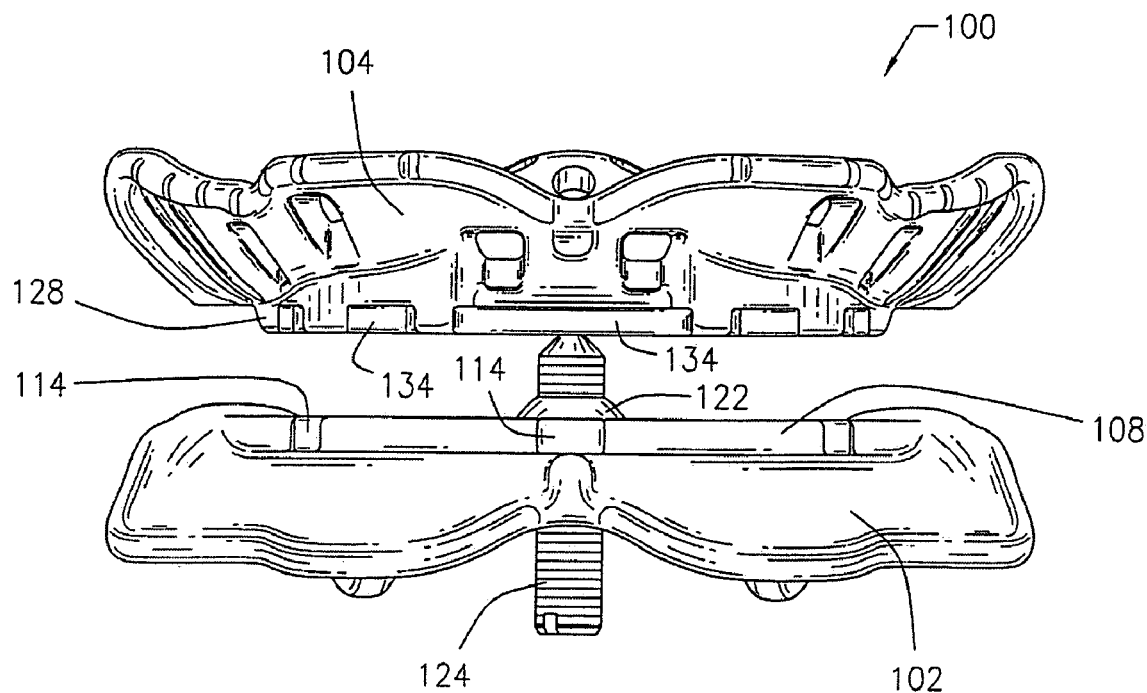
FIG. 4 is an anterior perspective view of the integrated modular dental measuring apparatus shown in FIG. 1.
Figure 5:
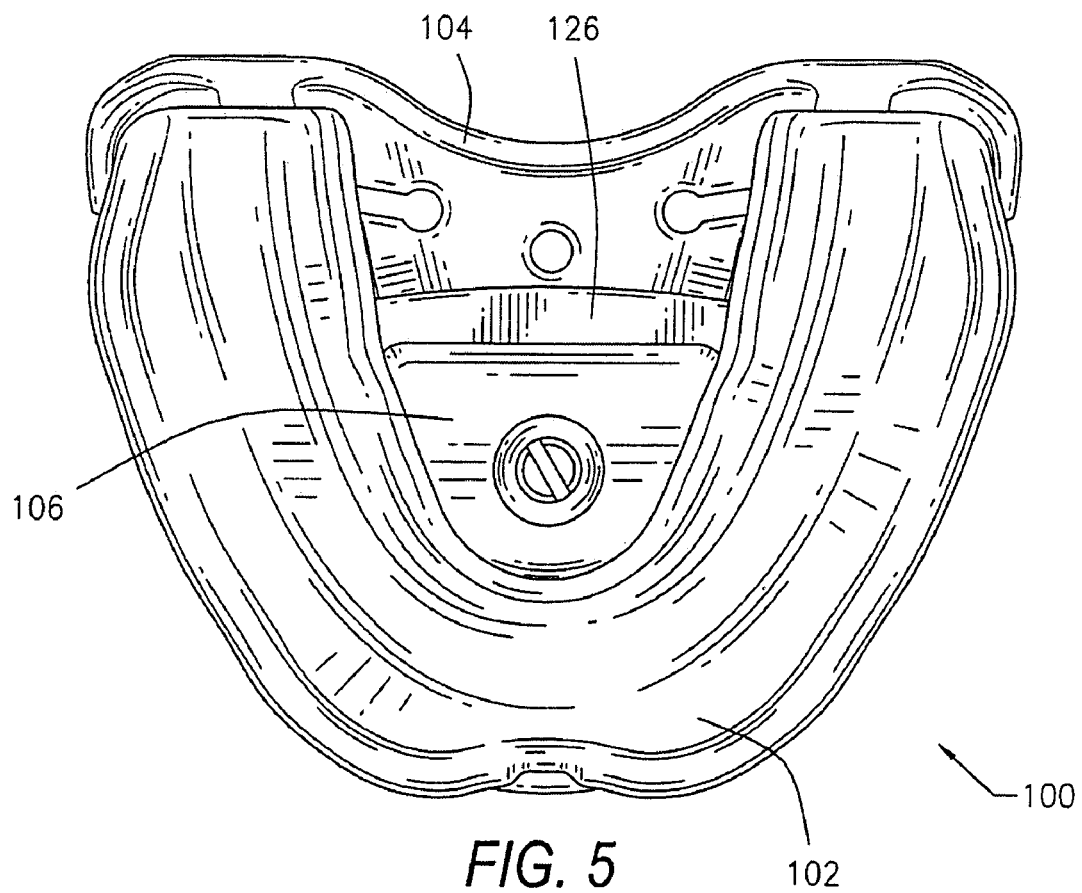
FIG. 5 is a bottom perspective view of the integrated modular dental measuring apparatus shown in FIG. 1.

As illustrated in FIGS. 1 though 5 and 8 through 10, the upper dental tray 104 of the integrated modular dental measuring apparatus 100 may include a plurality of body openings 152 at predetermined locations. The body openings 152 have a variety of sizes, shapes and orientations depending on where they are located in the upper dental tray 104. In addition, a border 154 may be positioned along a terminal end of the periphery of the upper dental tray 104. The border 154 is substantially annular in shape having a plurality of border channels 156. The border 154 has a predetermined diameter such that the diameter of the border 154 is slightly larger that the thickness of the upper dental tray 104. Border channels 156 comprise substantially V-shaped cuts or notches. The plurality of border channels 156 may be positioned perpendicular to the border 154 at predetermined locations.

The upper dental tray 104 may be made to accommodate different sizes of mouths; for example, the upper dental tray 104 may come in small, medium and large sizes. However, every size of upper dental tray 104 has the same size ridge 128 and slots or gaps 132 at the same locations, so that one size of striking plate 126 fits into all sizes of the upper dental tray 104. This reduces the required inventory of striking plates 126.

As illustrated in FIG. 10, the combination of the adjustable post 124, the rotatable ball nut 122 and the striking plate 126 on the upper dental tray 104 are utilized to obtain and establish proper occlusal vertical and centric relation positions. By adjusting the length and the angular position of the post 124, thereby varying the location at which the post 124 contacts the striking plate 126, proper occlusal vertical and centric relation between the lower dental tray 102 and the upper dental tray 104 of the integrated modular dental measuring apparatus 100 may be obtained and established. The occlusal device for diagnostic evaluation is described in detail in Applicant's co-pending application Ser. No. 11/754,009, which is incorporated herein by reference. Additionally, the post 124 and ball nut 122 may be removed from the lower dental tray 102 and the contact plate 106 may be used as a spacer between the upper dental tray 104 and the lower dental tray 102.

Once the desired positions have been established, the upper dental tray 104 and the lower dental tray 102 of the integrated modular dental measuring apparatus 100 may be removed. A third set of dental trays may then be utilized to take an impression of the patient's lips and mouth and to determine the patient's tongue, cheek, and lip positioning. The third set of dental trays may be the same lower tray 102 and upper tray 104 used in the previously described procedure without the contact plate or striking plate. Other such dental trays and usage is explained in detail in Applicant's co-pending application Ser. No. 60/986,142, which is incorporated herein by reference.

Figure 11:
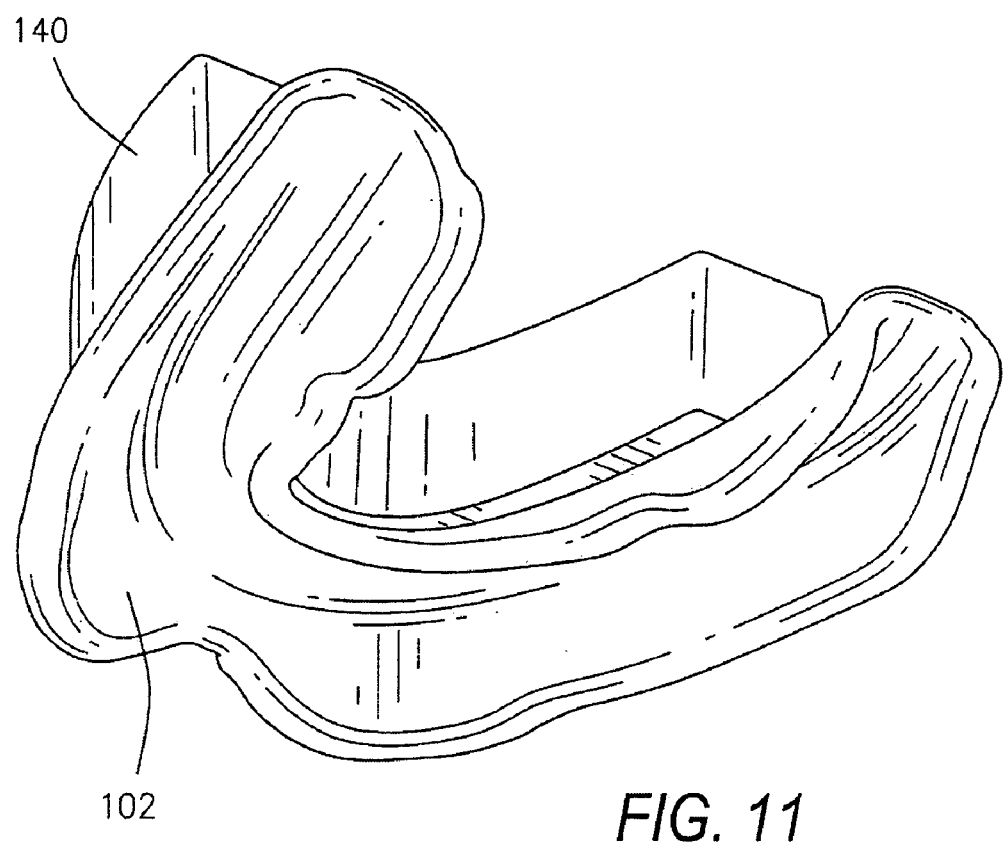
FIG. 11 is a perspective view of an example of a upper impression tray seated on a lower dental tray in accordance with an illustrative embodiment of the integrated modular dental measuring apparatus and method for dentures disclosed herein.
Figure 12:
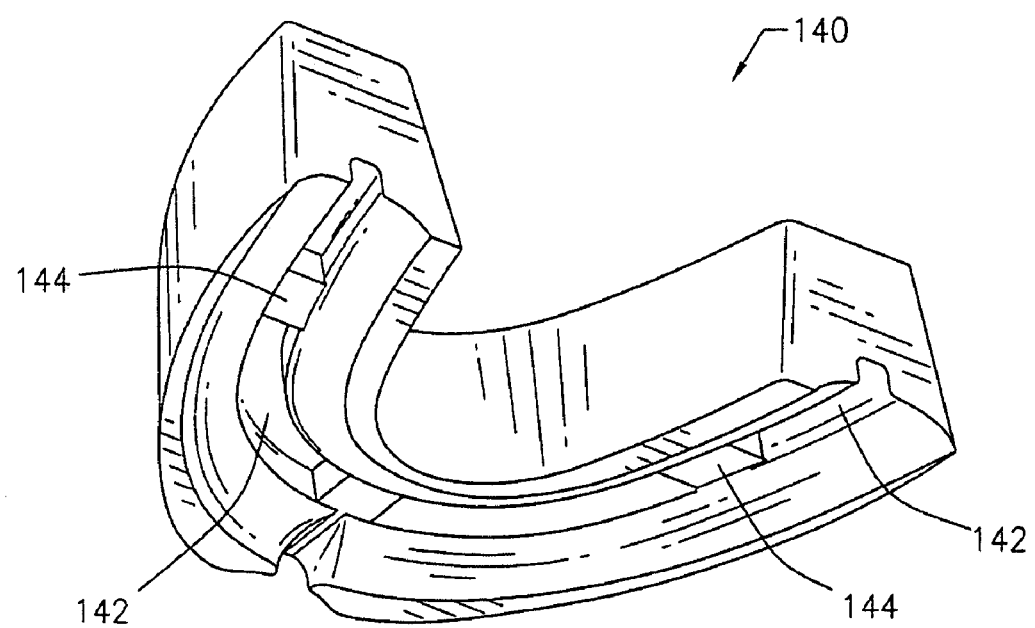
FIG. 12 is a perspective view of an example of the upper impression tray shown in FIG. 11.

As exemplified in FIGS. 11 and 12 and with the contact plate 106 removed from the lower dental tray 102, the lower dental tray 102 may be seated onto a preformed upper impression tray 140. The upper impression tray 140 may be formed of any suitable dental impression material, such as wax or resin. The upper impression tray 140 may be preformed to fit onto the lower tray 102. FIG. 12 illustrates the upper impression tray 140 having channels 142 for receipt of the upwardly extending ridge 108 running along the top surface 110 of the lower dental tray 102. The channel 142 of the upper impression tray 140 can include stubs 144, which may be sized to frictionally engage the gaps 112 of the ridge 108 of the lower dental tray 102.

During a procedure known as esthetic blue printing, the shape of the patient's upper lip and mouth are recognized in the upper impression tray 140, which may be preheated slightly prior to insertion into the oral cavity of the patient. The combination of the lower dental tray 102 and the upper impression tray 140 is then inserted into the oral cavity of the patient. Once the shape of the patient's upper lip and mouth are registered with the upper impression tray 140, the lower dental tray 102 and the upper impression tray 140 are removed from the patient's mouth.

Figure 13:
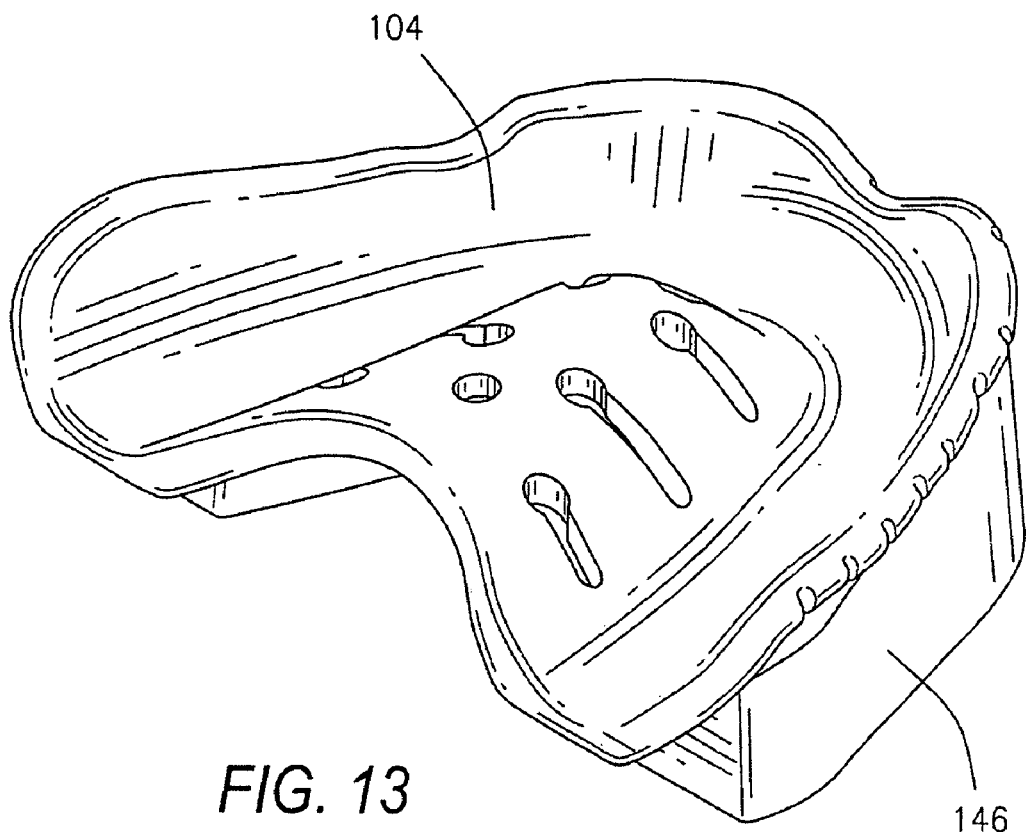
FIG. 13 is an elevated perspective view of an example of a lower impression tray seated on a upper dental tray in accordance with an illustrative embodiment of the integrated modular dental measuring apparatus and method for dentures disclosed herein.
Figure 14:
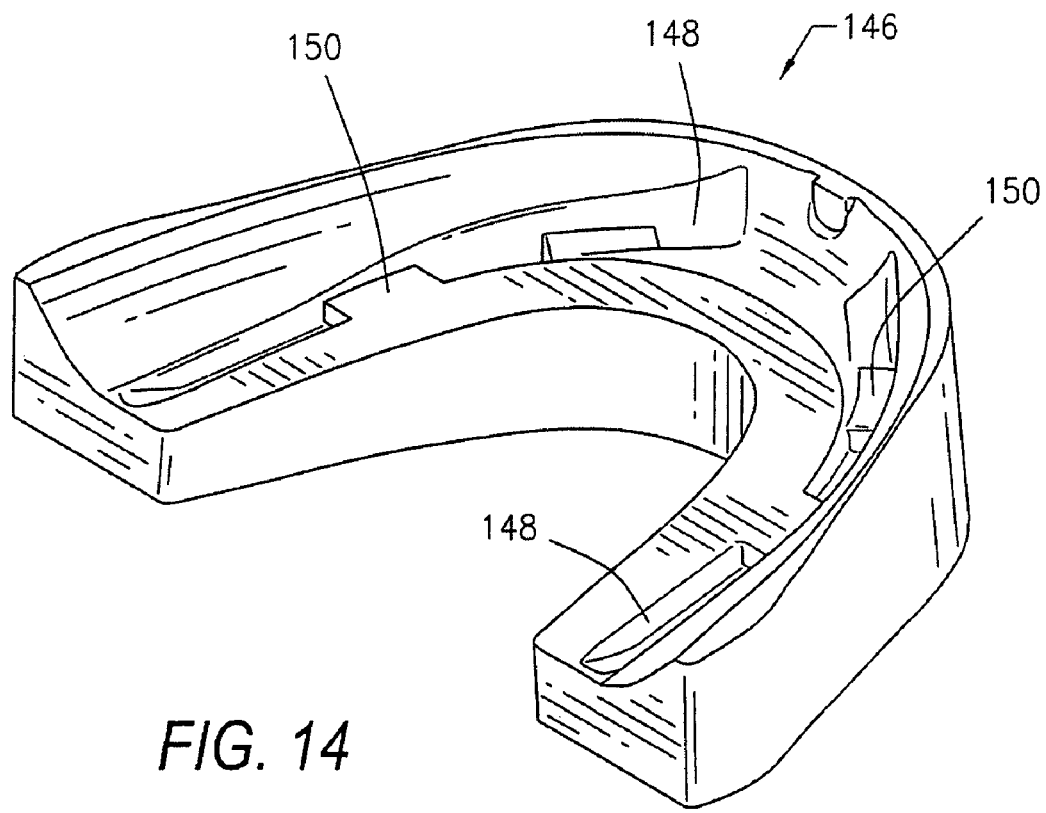
FIG. 14 is a perspective view of an example of the lower impression tray shown in FIG. 13.
Figure 15:
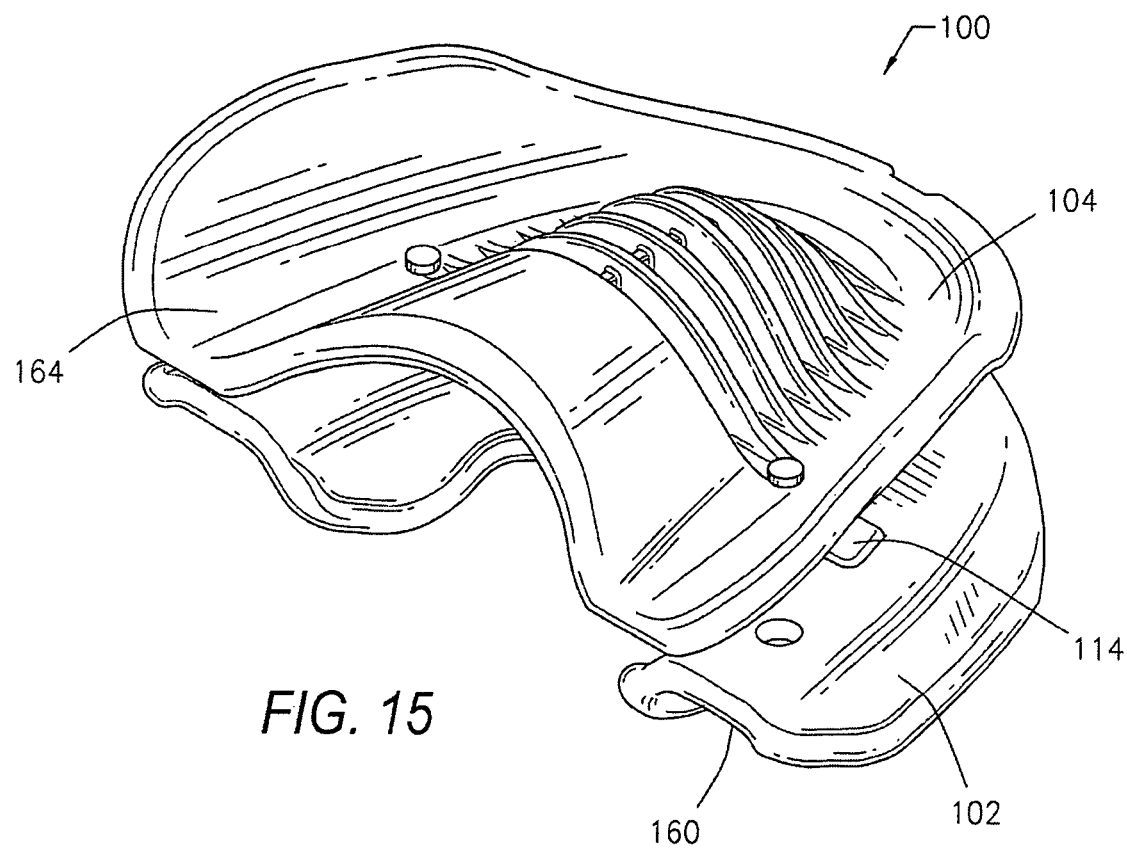
FIG. 15 is a perspective view of another example of an integrated modular dental measuring apparatus in accordance with an illustrative embodiment of the integrated modular dental measuring apparatus and method for dentures disclosed herein.
Figure 16:
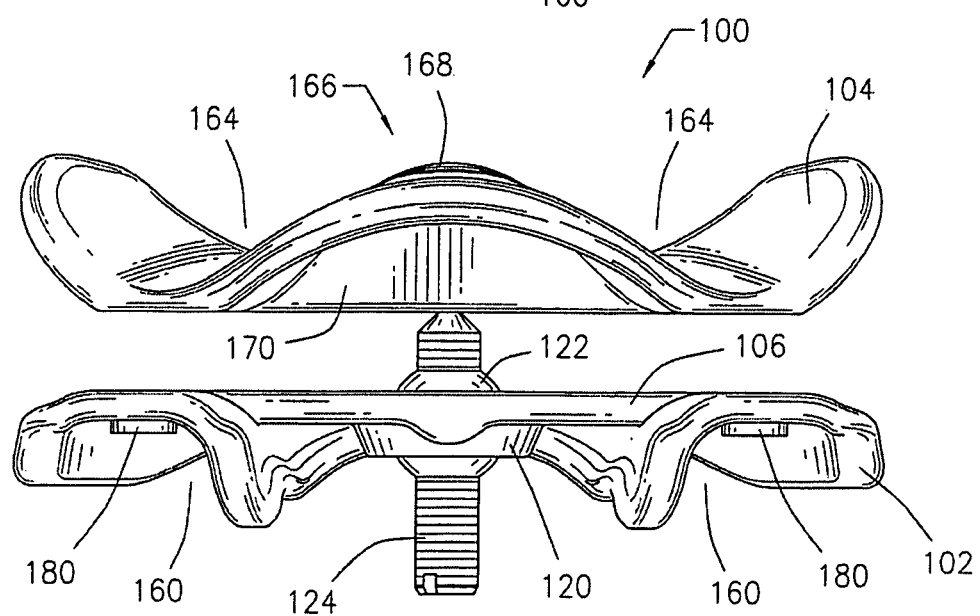
FIG. 16 is a posterior perspective view of the integrated modular dental measuring apparatus shown in FIG. 15.
Figure 17:
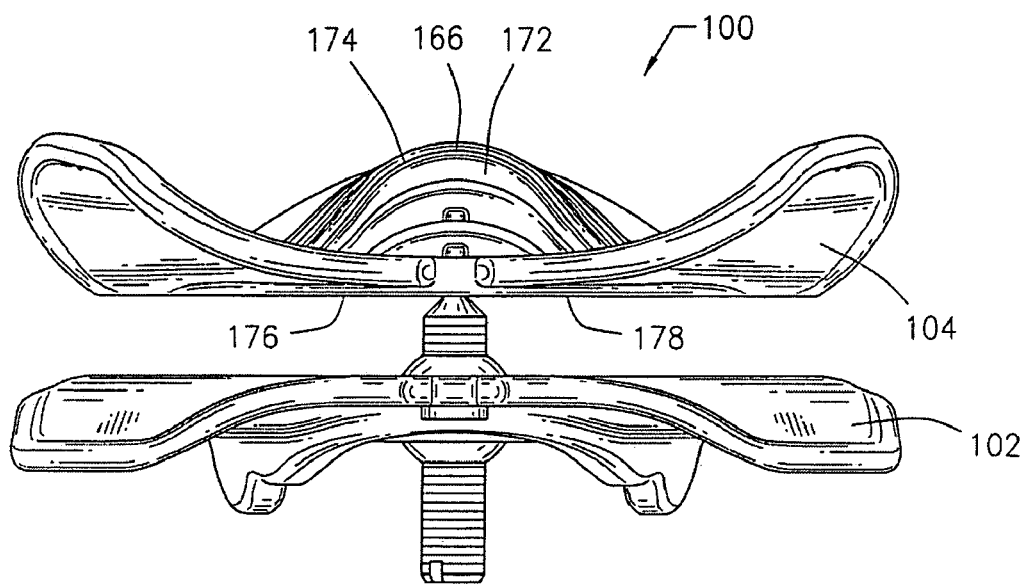
FIG. 17 is an anterior perspective view of the integrated modular dental measuring apparatus shown in FIG. 15.
Figure 18:
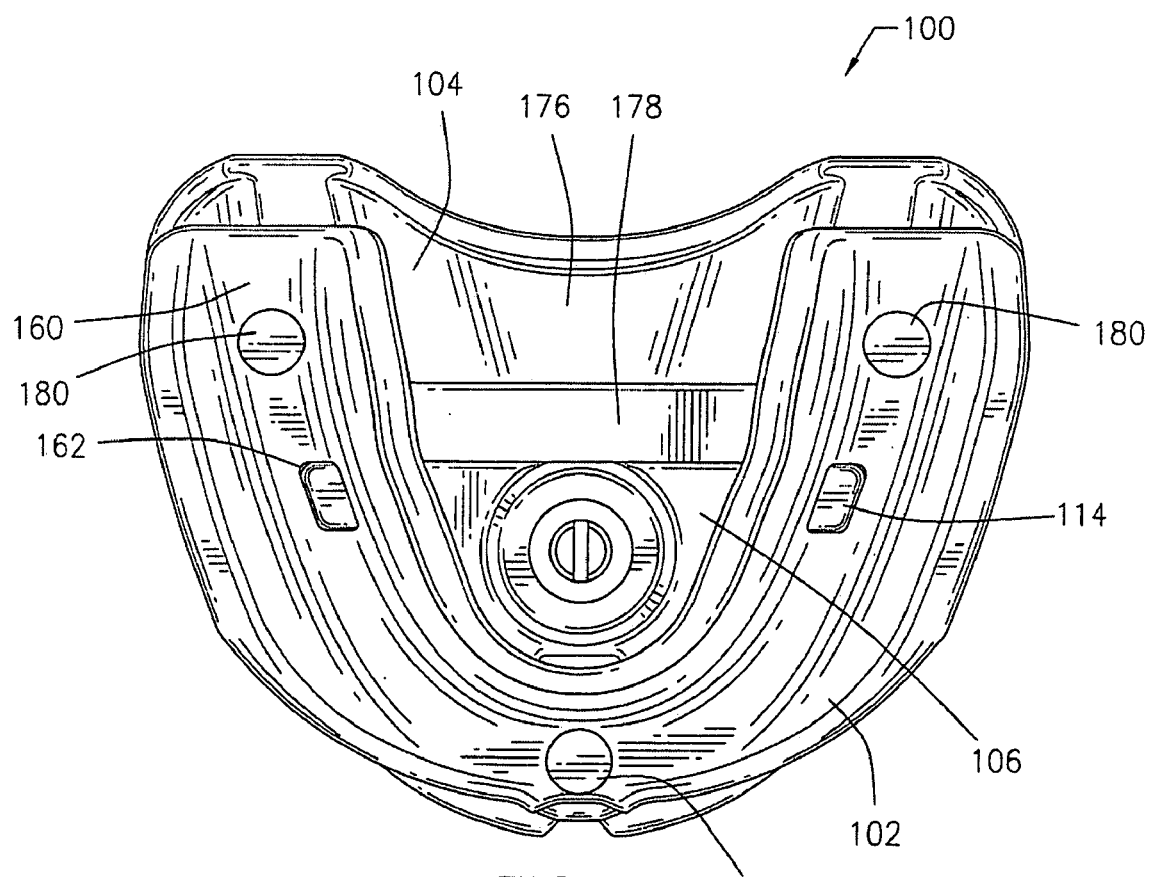
FIG. 18 is a bottom perspective view of the integrated modular dental measuring apparatus shown in FIG. 15.
Figure 19:
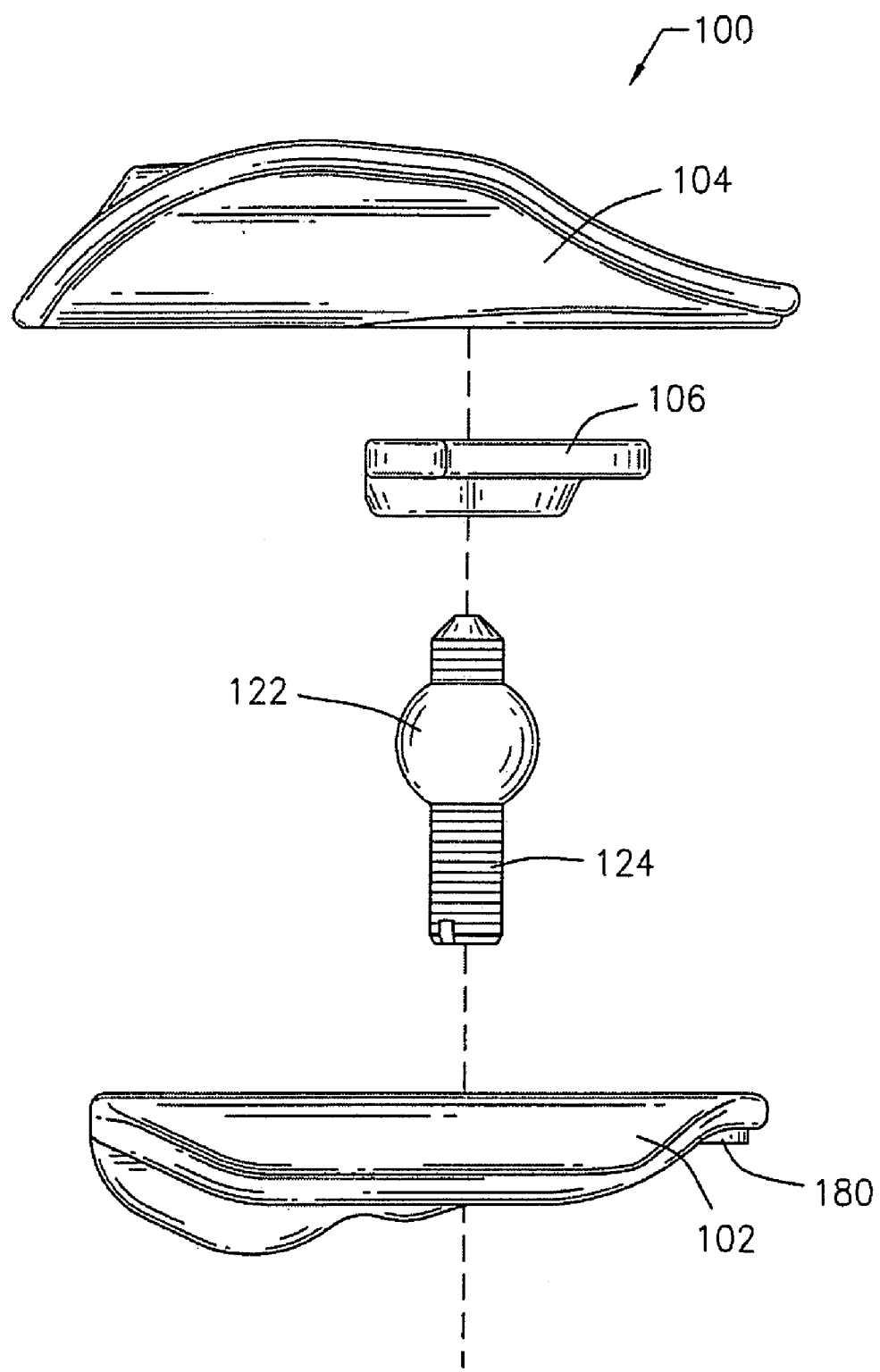
FIG. 19 is an exploded perspective view of the integrated modular dental measuring apparatus shown in FIG. 15.

With the striking plate 126 removed from the upper dental tray 104, as shown in FIG. 13, a lower impression tray 146 may be seated on the downwardly extending ridge 128 running along a bottom surface 130 of the upper dental tray 104. As illustrated in FIG. 14, the lower impression tray 146 may include channel 148 and stubs 150 to respectively mate with the ridge 128 on the upper dental tray 104. Similar to the upper impression tray 140, the lower impression tray 146 may be constructed of any suitable moldable dental composition, such as wax or resin.

Using a neutral zone technique, the lower impression tray 146 and the upper dental tray 104 are inserted into the oral cavity of the patient in order to determine the shape of the patient's lower lip and mouth and to determine the patient's tongue, cheek, and lip positioning. The lower impression tray 146 may be preheated, and once the lower impression tray 146 registers the particular portions of the patient's oral cavity, the upper dental tray 104 and the lower impression tray 146 are removed.

Figure 20:
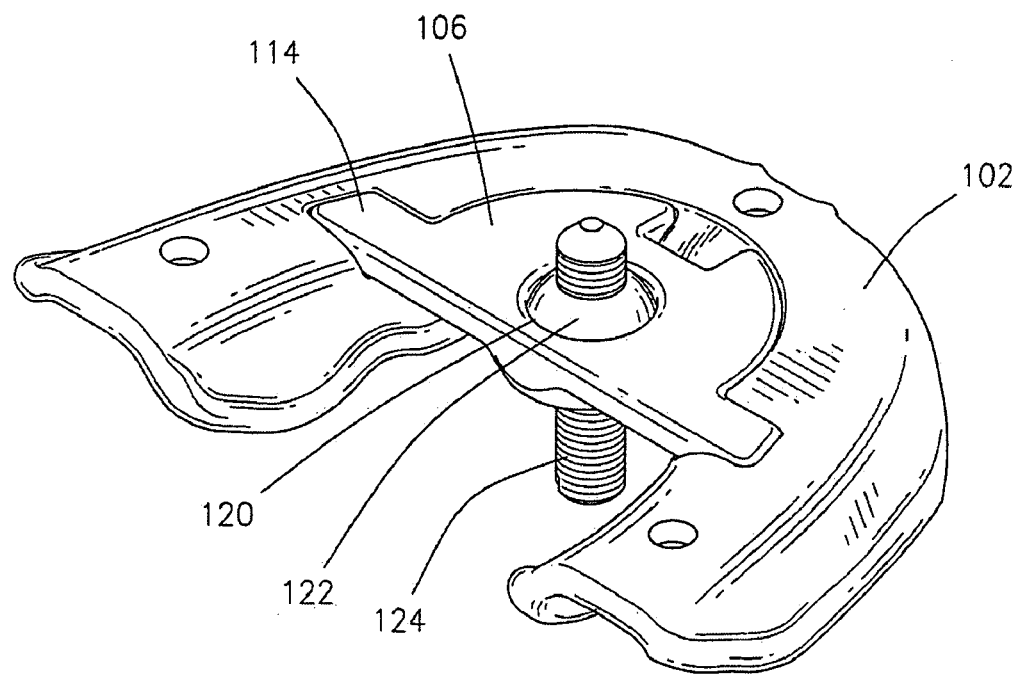
FIG. 20 is a top perspective view of an example of a lower dental tray with a contact plate inserted thereon in accordance with an illustrative embodiment of the integrated modular dental measuring apparatus and method for dentures disclosed herein.
Figure 21:
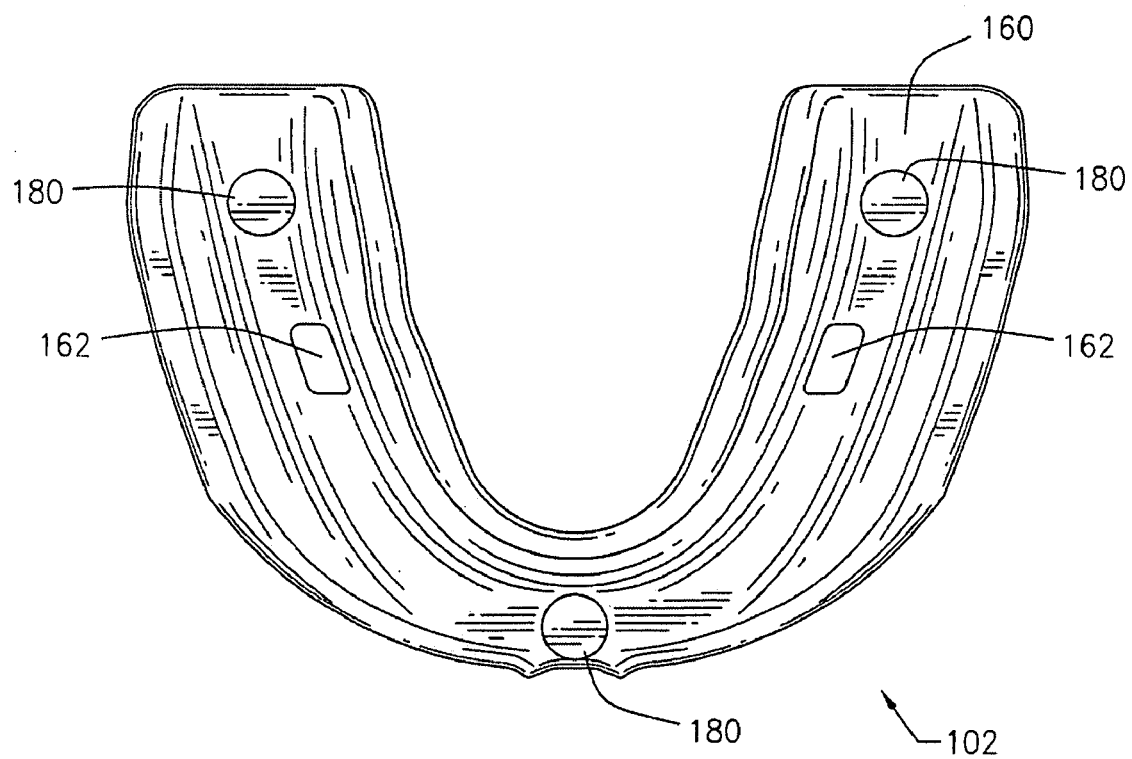
FIG. 21 is a bottom perspective view of the lower dental tray shown in FIG. 20 with the contact plate removed.

By way of another example the integrated modular dental measuring apparatus 100 may comprise the lower dental tray 102 and the upper dental tray 104 as exemplified in FIGS. 15 through 19. The lower dental tray 102 includes a contact plate 106 removably secured to and attached to the lower dental tray 102. The lower dental tray 102 may be arcuate in form and includes an arched intaglio channel 160 for receipt of the patient's lower teeth. The intaglio channel 160 of the lower dental tray 102 may include at least one retention post 180 to aid in retaining an impression material (not shown). Small apertures 162 may be formed at various points along the intaglio channel 160 of the lower dental tray 102, such as on opposing arches as illustrated. Into the apertures 162 fit a plurality of tabs 114 extending outward from the contact plate 106 on corresponding locations, such as the side portions 118 of the contact plate 106. The tabs 114 may be slightly larger than the apertures 162 so that the tabs 114 snugly fit therein. Thus, the contact plate 106 snap fits into place on the lower dental tray 102. Accordingly, the lower dental tray 102 may be used with or without the contact plate 106. FIG. 20 illustrates the lower dental tray 102 with the contact plate 106 attached thereto apart from the upper dental tray 104 to be described herein, while FIG. 21 illustrates the lower dental tray 102 with the contact plate 106 removed, with the apertures 162 visible.

The lower dental tray 102 may be made in varying sizes to accommodate different sizes of mouths. For example, the lower dental tray 102 may come in small, medium and large sizes. However, every size of lower dental tray 102 has the apertures 162 at the same locations, so that one size of contact plate 106 fits into all sizes of lower dental tray 102 thereby reducing the required inventory of contact plates 106.

The contact plate 106 includes a tapered opening 120, and a ball nut 122 is retained in the tapered opening 120 to permit the ball nut 122 to rotate within the tapered opening 120. The ball nut 122 may be spherical in shape and may have a cylindrical bore through a diameter thereof. A post 124 is adjustably secured to the ball nut 122 so that the length and the angular position of the post 124 may be altered.

Figure 22:
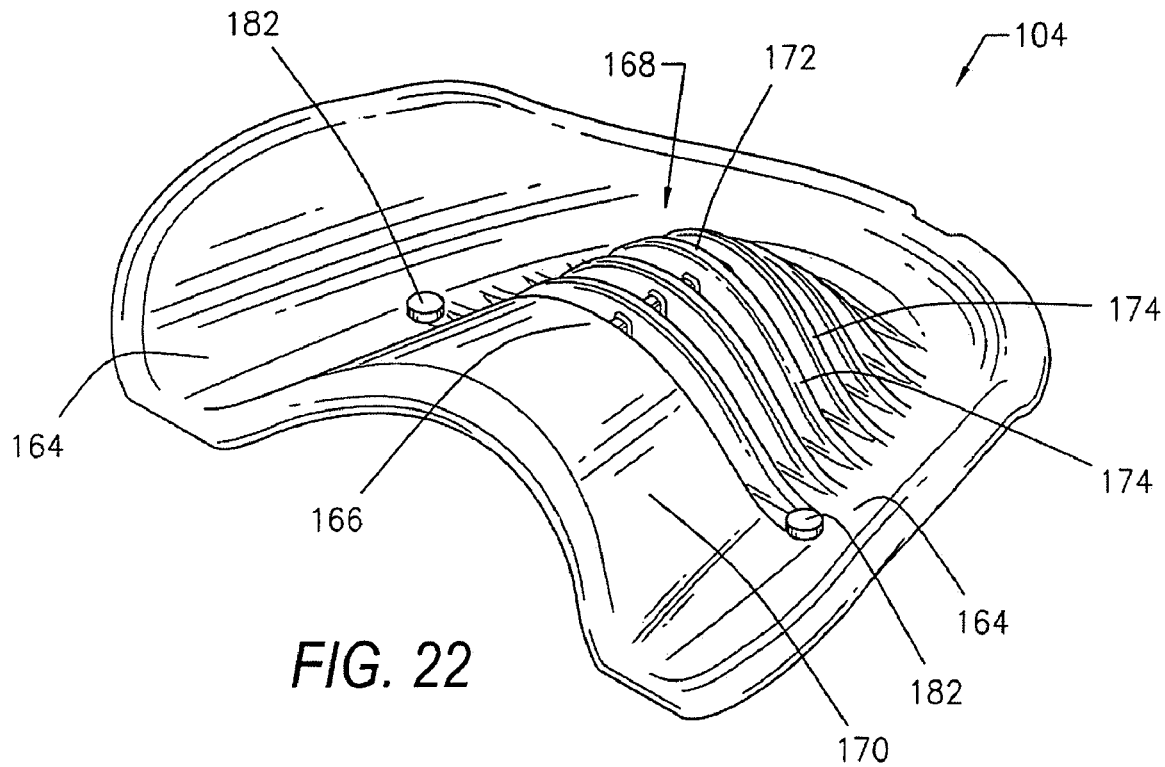
FIG. 22 is a top perspective view of an example of an upper dental tray in accordance with an illustrative embodiment of the integrated modular dental measuring apparatus and method for dentures disclosed herein.
Figure 23:
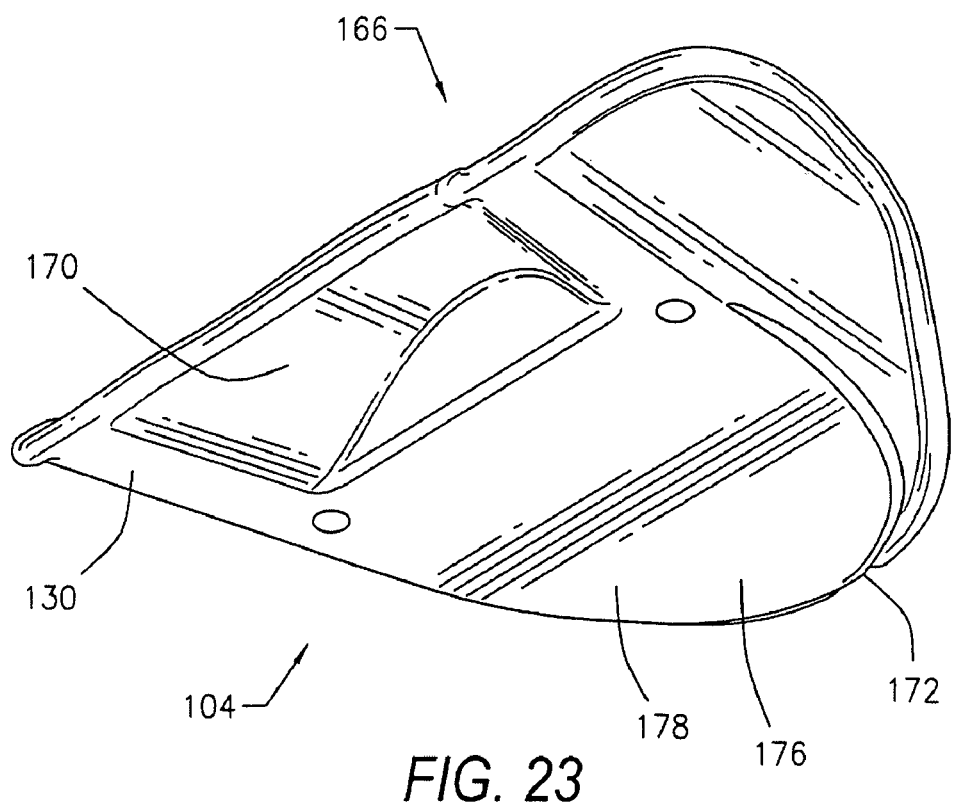
FIG. 23 is a bottom perspective view of the upper dental tray as shown in FIG. 22.

Returning to consideration of FIGS. 15 through 19, the upper dental tray 104 includes an arched intaglio channel 164 for receipt of the patient's upper teeth and an upwardly contoured palatal ledge 166 spanning the arches of the intaglio channel 164. The intaglio channel 164 of the upper dental tray 104 may include at least one retention post 182 to aid in retaining an impression material (not shown). As shown in FIG. 22, an upper surface 168 of the palatal ledge 166 may include a smooth, posterior portion 170 and an anterior portion 172 having a plurality of substantially vertical and parallel fins 174. As shown in FIG. 23, a bottom surface 176 of the palatal ledge 166 may include a substantially planar striking sector 178 near the anterior portion 172, which is coplanar with the bottom surface 130 of the intaglio channel 164 of the upper dental tray 104. The posterior end 170 of the bottom surface 176 of the palatal ledge 166 is substantially curved for capturing the hard-soft throat palate of the patient and accommodates the sublingual gland and fatty tissue of the mylohyoid space. The upper dental tray 104 may be made to accommodate different sizes of mouths; for example, the upper dental tray 104 may come in small, medium and large sizes.

The combination of the adjustable post 124, the rotatable ball nut 122 and the striking sector 178 on the upper dental tray 104 are utilized to obtain and establish proper occlusal vertical and centric relation positions. By adjusting the length and the angular position of the post 124 thereby varying the location at which the post 124 contacts the striking plate 126, the proper occlusal vertical and centric relation between the lower dental tray 102 and the upper dental tray 104 of the integrated modular dental measuring apparatus 100 may be obtained and established. Additionally, the post 124 and ball nut 122 may be removed from the lower dental tray 102 and the contact plate 106 may be used as a spacer between the upper dental tray 104 and the lower dental tray 102.

Utilizing the foregoing sets of measurements and calibrations, an accurate set of dentures may be produced. A cast impression (not shown), which may be formed at any time following the use of the first set of dental trays, may be combined with the upper and lower dental trays 102 and 104 of the integrated modular dental measuring apparatus 100 disclosed herein. Using an articulator (not shown) in conjunction with the occlusal vertical and centric relation positions obtained and registered with the integrated modular dental measuring apparatus 100, the cast impression may be related to ensure proper positioning of the arches with respect to the jaw of the patient. The integrated modular dental measuring apparatus 100 may be used for multiple measurements and calibrations. In addition, all of the foregoing measurements and calibrations may be taken in a single visit to a dentist or technician.

Whereas, the apparatuses and methods have been described in relation to the drawings and claims, it should be understood that other and further modifications, apart from those shown or suggested herein, may be made within the spirit and scope of this invention.

What is claimed is:

1. An integrated modular dental measuring apparatus, comprising:
   a lower dental tray having a rigid, preformed, upwardly extending, elongate ridge running along a top surface, wherein said ridge having preformed periodic gaps at predetermined locations, said lower dental tray having a border positioned along a terminal end of the periphery of the lower dental tray, said border being substantially annular in shape and having a predetermined diameter slightly greater than the thickness of the lower dental tray;
   a contact plate with outwardly extending tabs sized and spaced such that said tabs fit within said gaps in said ridge of said lower dental tray and allow said contact plate to snap onto said lower dental tray;
   a tapered, generally spherical opening through said contact plate;

a generally spherical ball nut rotatably retained in said tapered opening through said contact plate, said ball nut having a cylindrical bore through a diameter thereof;

a threaded post adjustably secured in said cylindrical bore of said ball nut, said post having an upper length and a lower length that extend beyond said ball nut;

an upper dental tray having a rigid, preformed, downwardly extending, elongate ridge running along a bottom surface, said ridge having preformed periodic gaps at predetermined locations, said upper dental tray having a border positioned along a terminal end of the periphery of the upper dental tray, said border being substantially annular in shape and having a predetermined diameter slightly greater than the thickness of the upper dental tray, said upper dental tray having a plurality of body openings at predetermined locations; and a striking plate with outwardly extending tabs sized and spaced such that said tabs fit within said gaps in said ridge of said upper dental tray and allow said striking plate to snap onto said upper dental tray; and wherein the combination of said contact plate, said ball nut, and said post with said striking plate cooperate to obtain occlusal vertical dimension, centric relation position, and other dental measurements.

2. The integrated modular dental measuring apparatus of claim 1 wherein said contact plate functions as a spacer when said post and said ball nut are removed during usage.

3. The integrated modular dental measuring apparatus of claim 1 wherein said contact plate and said striking plate are capable of being removed respectively enabling said lower dental tray to obtain functional position and said upper dental tray to obtain esthetic blue printing.

4. The integrated modular dental measuring apparatus of claim 1 further comprising an upper impression tray having a channel for receipt of said ridge of said lower dental tray and a lower impression tray having a channel for receipt of said ridge on said upper dental tray.

5. The integrated modular dental measuring apparatus of claim 4 wherein said channel of said upper impression tray include stubs sized to frictionally engage said gaps in said ridge of said lower dental tray.

6. The integrated modular dental measuring apparatus of claim 4 wherein said channel of said lower impression tray include stubs sized to frictionally engage said gaps in said ridge of said upper dental tray.

7. The integrated modular dental measuring apparatus of claim 4 wherein said upper impression tray and said lower impression tray are formed of wax or resin.

8. The integrated modular dental measuring apparatus of claim 1 wherein said lower dental tray and said upper dental tray are modular and convertible.

9. The integrated modular dental measuring apparatus of claim 1 wherein said body openings in said upper dental tray have a variety of sizes, shapes and orientations.

10. The integrated modular dental measuring apparatus of claim 1 wherein said border of said upper dental tray has a plurality of border channels comprising substantially V-shaped cuts or notches.

11. The integrated modular dental measuring apparatus of claim 10 wherein said border channels are positioned substantially perpendicularly to said border at predetermined locations.

12. An integrated modular dental measuring apparatus, comprising:

a lower dental tray having a plurality of apertures along an arched intaglio channel, said apertures comprising at least a pair of opposing apertures on each arch of said intaglio channel, a top surface of said lower dental tray being substantially planar, said lower dental tray having a border positioned along a terminal end of the periphery of the lower dental tray, said border being substantially annular in shape and having a predetermined diameter slightly greater than the thickness of the lower dental tray;

a contact plate with outwardly extending opposing tabs sized and spaced such that said tabs fit within said opposing apertures of said lower dental tray and allow said contact plate to snap onto said lower dental tray;

a tapered, generally spherical opening through said contact plate;

a generally spherical ball nut rotatably retained in said tapered opening through said contact plate, said ball nut having a cylindrical bore through a diameter thereof;

a threaded post adjustably secured in said cylindrical bore of said ball nut, said post having an upper length and a lower length that extend beyond said ball nut;

an upper dental tray being unitary in construction and having a substantially planar striking sector on a bottom surface thereof, said upper dental tray having an arched intaglio channel and an upwardly contoured palatal ledge spanning said intaglio channel, said upper dental tray having a border positioned along a terminal end of the periphery of the upper dental tray, said border being substantially annular in shape and having a predetermined diameter slightly greater than the thickness of the upper dental tray; and wherein the combination of said contact plate, said ball nut, and said post with said striking sector cooperate to obtain occlusal vertical dimension, centric relation position, and other dental measurements.

13. The integrated modular dental measuring apparatus of claim 12 wherein said contact plate functions as a spacer when said post and said ball nut are removed during usage.

14. The integrated modular dental measuring apparatus of claim 12 said palatal ledge includes an upper surface having a smooth, posterior portion and an anterior portion having a plurality of substantially vertical and parallel fins to aid in retaining an impression material.

15. The integrated modular dental measuring apparatus of claim 12 wherein said palatal ledge includes a bottom surface having a substantially curved posterior portion for capturing the hard-soft throat palate and accommodating the sublingual gland and fatty tissue of the mylohyoid space of a patient and said striking sector near an anterior portion, which is coplanar with said bottom surface of said intaglio channel of said upper dental tray.

16. The integrated modular dental measuring apparatus of claim 12 wherein said lower dental tray and said upper dental tray are modular and convertible.

17. The integrated modular dental measuring apparatus of claim 12 further comprising at least one protruding, preformed retention post projecting outwardly from each arch of said intaglio channel of said lower dental tray and said upper dental tray to aid in retaining an impression material.

* * * * *